(12) United States Patent
Bauer et al.

(10) Patent No.: US 10,327,585 B2
(45) Date of Patent: Jun. 25, 2019

(54) BREASTMILK HANDLING APPARATUS PARTICULARLY USEFUL FOR WARMING OF BREASTMILK CONTAINERS SUCH AS BOTTLES AND SYRINGES

(71) Applicant: Medela Holding AG, Baar (CH)

(72) Inventors: Ryan Bauer, Fox River Grove, IL (US); Amanda Miller, McHenry, IL (US); Jill M. Hunt, Woodstock, IL (US); Joseph Wach, Ingleside, IL (US)

(73) Assignee: Medela Holding AG (CH)

( * ) Notice: Subject to any disclaimer, the term of this patent is extended or adjusted under 35 U.S.C. 154(b) by 1136 days.

(21) Appl. No.: 14/470,446

(22) Filed: Aug. 27, 2014

(65) Prior Publication Data

US 2014/0374371 A1 Dec. 25, 2014

Related U.S. Application Data

(62) Division of application No. 12/371,834, filed on Feb. 16, 2009, now Pat. No. 9,241,596.

(60) Provisional application No. 61/066,186, filed on Feb. 19, 2008.

(51) Int. Cl.
*A47J 36/24* (2006.01)
*A47J 39/00* (2006.01)
*A61J 9/00* (2006.01)
*B65D 25/02* (2006.01)
*A47J 36/04* (2006.01)

(52) U.S. Cl.
CPC ......... *A47J 36/2433* (2013.01); *A47J 39/003* (2013.01); *A61J 9/001* (2013.01); *B65D 25/02* (2013.01); *A47J 36/04* (2013.01)

(58) Field of Classification Search
CPC ............... A47J 36/2411; A47J 36/2433; A47J 36/2483; A47J 39/003; A61J 9/01
USPC .................................................. 220/741, 737
See application file for complete search history.

(56) References Cited

U.S. PATENT DOCUMENTS

| 1,865,472 A | 7/1932 | Lamstein |
| 2,090,666 A | 8/1937 | Copeland |
| 2,187,196 A | 1/1940 | Douglass |

(Continued)

FOREIGN PATENT DOCUMENTS

| EP | 0036612 A1 | 9/1981 |
| WO | WO 02/31417 A1 | 4/2002 |
| WO | WO 05/041733 A1 | 5/2005 |

OTHER PUBLICATIONS

International Search Report for PCT/US09/34303 dated Jan. 25, 2010.

*Primary Examiner* — Andrew T Kirsch
(74) *Attorney, Agent, or Firm* — McDonnell Boehnen Hulbert & Berghoff LLP

(57) ABSTRACT

The present invention relates to an infant feeding warming system useful to repeatedly and precisely warm breastmilk or formula for use in the NICU. The system in one form comprises a bedside unit that is attachable to an IV pole. The system may also comprise a centralized warming station with multiple chambers, wherein one chamber heats a bottle or syringe, and the remaining chambers are used for storage and/or refrigeration. The system will use a non-liquid heating system to heat feedings. A disposable liner may be used inside the chamber. The system may also contain heating algorithms that are based on a user inputting milk parameters such as volume and initial temperature.

10 Claims, 17 Drawing Sheets

(56) References Cited

U.S. PATENT DOCUMENTS

| | | | |
|---|---|---|---|
| 2,292,992 A | | 8/1942 | Lawrence |
| 2,413,176 A | | 12/1946 | Deaton |
| 2,428,996 A | | 10/1947 | Schworm, Jr. |
| 2,583,118 A | | 1/1952 | Porambo |
| 2,584,435 A | | 2/1952 | Doerr |
| 2,595,685 A | | 5/1952 | Mallory |
| 2,644,072 A | | 6/1953 | Aruth |
| 2,653,214 A | | 9/1953 | Shaw |
| 2,654,018 A | | 9/1953 | Bugge |
| 2,713,112 A | | 7/1955 | Mills |
| 3,346,883 A | * | 10/1967 | Ersek ................ A61B 10/0038 383/11 |
| 4,966,303 A | * | 10/1990 | Jones ................ A47G 23/0266 215/13.1 |
| 5,531,810 A | | 7/1996 | Fullemann |
| 5,817,146 A | | 10/1998 | Augustine |
| 5,954,431 A | * | 9/1999 | Fabel .................... B42D 15/08 229/313 |
| 6,294,762 B1 | | 9/2001 | Farles, Jr. et al. |
| 6,617,552 B1 | | 9/2003 | Taylor |
| 8,087,528 B1 | * | 1/2012 | Scarlett ............. A47G 23/0216 220/23.89 |
| 2008/0093357 A1 | * | 4/2008 | Norman ............. A47J 36/2433 219/521 |

\* cited by examiner

BREASTMILK HANDLING APPARATUS PARTICULARLY USEFUL FOR WARMING OF BREASTMILK CONTAINERS SUCH AS BOTTLES AND SYRINGES

CROSS-CITE TO RELATED APPLICATIONS

This application is a divisional application of U.S. patent application Ser. No. 12/371,834, filed Feb. 16, 2009, which claims priority to U.S. Provisional Application Ser. No. 61/066,186, filed on Feb. 19, 2008. The disclosures of application Ser. No. 12/371,834 and 61/066,186 are incorporated herein by reference in their entirety for all purposes.

FIELD OF THE INVENTION

This invention relates generally to a warming, as well as cooling, system and apparatus, particularly useful for breastmilk, and most particularly for neonatal care.

BACKGROUND

Most infants in the neonatal intensive care unit (NICU) are not able to breastfeed effectively. Instead, either the infant is bottle fed, or breastmilk or formula is delivered through an orogastric or nasogastric passage to the infant's stomach. In these situations, breastmilk is expressed from the mother and stored in a freezer or refrigerator until it is desired for use, at which point it is often transferred to bottles or syringes for delivery to the baby.

Because infants in the NICU have difficulty maintaining their body temperature, the breastmilk or formula is warmed prior to feeding so the chill will not stress the infant. The current practice for warming breastmilk or formula is for nurses to place the bottles in warm water baths. The water in the warm water baths is typically supplied from sink faucets. Depending on the hot water settings, distance of the NICU from the water heater, and other variables, the temperatures of the warm water can vary greatly. The temperatures of the warm water can also vary depending on how long the nurses wait for the water to reach its maximum temperature before filling the baths. The actual water temperature is not measured, and the actual temperature of the milk in the bottle is unknown.

The breastmilk is typically thawed using one of several methods: thawing for more than 24 hours in a refrigerator at 4° C., setting the liquid out for an undetermined number of hours on a counter at room temperature and then placing it in a refrigerator, or a rapid thaw may be performed in which the protocol used for thawing and warming with water is employed to frozen milk in order to accelerate the thawing rate. This protocol is an uncontrolled method in which the damage that has potentially been done to the milk as a result of the temperature and rate times that are employed is unknown.

Additionally, the prevention of the spreading of germs is critical in this environment, as infants in the NICU are very fragile and susceptible to infection. The risk of warming a bottle or syringe using water that is not sterile and contains some level of bacteria exists. This water could leak into the bottle or syringe and contaminate the liquid within, aid transfer of germs through handling of the water and containers, and provide a media for further bacterial growth. This is a known potential of contamination within the majority of hospitals. Just using water as a temperature adjustment medium is considered undesirable.

The fact that water is used to heat the bottles and the bottles are then often carried to the baby's bed may also result in water damage to bedside charts and computers.

It is desirable to have an apparatus that can repeatedly warm and thaw breastmilk or formula to an appropriate temperature without detrimentally affecting the breastmilk composition in order to prevent stressing the infant and eliminating the risk of potential contamination sites. Conversely, it would be desirable for the same apparatus to further have a cooling (or refrigeration) aspect as well.

It is also desirable to perform these tasks as quickly as possible, given the time constraints and workload imposed upon neonatal nurses. Nurses usually state it takes them approximately 15 minutes for the total warming process for breastmilk. Considering that this task is repeated six to eight times a day, it can accumulate to a considerable amount of time and labor cost for a facility.

It is also desirable to have an apparatus that can handle all manner of devices that may be used to contain the breastmilk, such as syringes, bottles, jars, bags and other containers.

SUMMARY OF THE INVENTION

The present invention is an improved apparatus and system for thawing, warming and in a further application cooling, breastmilk. More particularly, the present invention has a principal objective of providing a bottle and syringe warmer system useful to repeatedly and precisely warm breastmilk or formula for use in the NICU, such as to infants in need of milk. It will be understood that while the invention is generally discussed in the particular environment of a bottle or syringe type container, and in the NICU setting, other containers and applications are contemplated and will fall within the scope of the invention.

The bottle and syringe warmer system in one form comprises a bedside unit that is attachable to an IV pole. By having the unit at a bedside IV pole, the amount of time a nurse is away from a baby due to milk preparation is greatly reduced. Warming and preparation is now done bedside, allowing nurses to spend more time devoted to the care of the patient. Additionally, every time milk is transferred from one area to another, a second nurse is typically required to verify that the right milk is going to the right patient. Enabling bedside preparation reduces the need for identification verification. The foregoing need not be pole-mounted, but could be a desktop unit.

Alternatively, or in addition, a bottle or syringe warming device may be a multi-port unit in a centralized milk preparation area. This embodiment comprises a centralized heating system that allows for the ability to warm and/or cool multiple containers at the same time while providing patient identification methods to properly identify each individual warming port. This embodiment would also provide all of the benefits of the single, IV-mountable unit: consistency, performance, safety, and reliability while reducing the cycle time spent by nurses, technicians, or other milk preparation staff in the thawing and warming of milk.

The bottle and syringe warming device is intended in a preferred form to accommodate a variety of sizes, shapes, and containers of various volumes commonly used in the NICU.

This device will most preferably use a non-liquid heating system to eliminate the risk of infection as well as cleanup associated with using water as a heat transfer means. The device will also preferably accommodate a liner element so as to capture spills and reduce potential contamination. The liner would be intended to be changed out between nurse shifts and patients, but may be changed more frequently as warranted. The liner may comprise a first material with an interior that defines a liquid containing portion and an opening defined by a perimeter. A top section that covers at least part of the opening may be made from a second material; the top section would contain an access port to the interior of the liquid containing portion.

The device will, in its preferred form, advantageously contain a heating algorithm or like operational feature based on a user inputting milk parameters such as volume and initial temperature. The heating program then provides for a predetermined thawing/warming cycle based upon the input parameters that yields a minimization of time required to heat milk with the least deleterious impact on the milk according to customized heat profiles. The apparatus will advantageously use a control heating and thawing cycle that has been designed, based on research, to not damage the critical composition of breastmilk or formula. For the nurse, mother, or other user, the input required is minimal and the rest is automated.

The bottle and syringe warming device will in its most preferred form herein use warm air forced convection as the primary mode of heat transfer. The air temperature will be regulated in accordance with the warming algorithm (program or other controller) associated with nurse/clinician input parameters. Temperature hold modes may further maintain desired temperatures until the user is ready to use the bottle or syringe (or other container).

In yet a further variation, the invention may advantageously further employ a cooling aspect. As discussed herein, for example, a Peltier heating/cooling element is employed, yielding the ability to readily switch between thawing/warming to cooling. A separate refrigeration element is also contemplated as a possibility.

All in all, a relatively compact apparatus and system is achieved by the invention which is adapted for use with a wide range of types, sizes, shapes and volumes of containers commonly employed in a hospital or other institutional setting for the handling of breastmilk. The foregoing invention is considered to be a highly useful apparatus and system for a NICU setting where a plurality of mothers and their premature babies are treated, and where the invention is easily operated and maintained with a minimum of effort and skill.

These and other advantages of the invention will be further understood upon consideration of the following detailed description of certain embodiments, taken in conjunction with the drawings, in which:

DETAILED DESCRIPTION

Figure 1A:
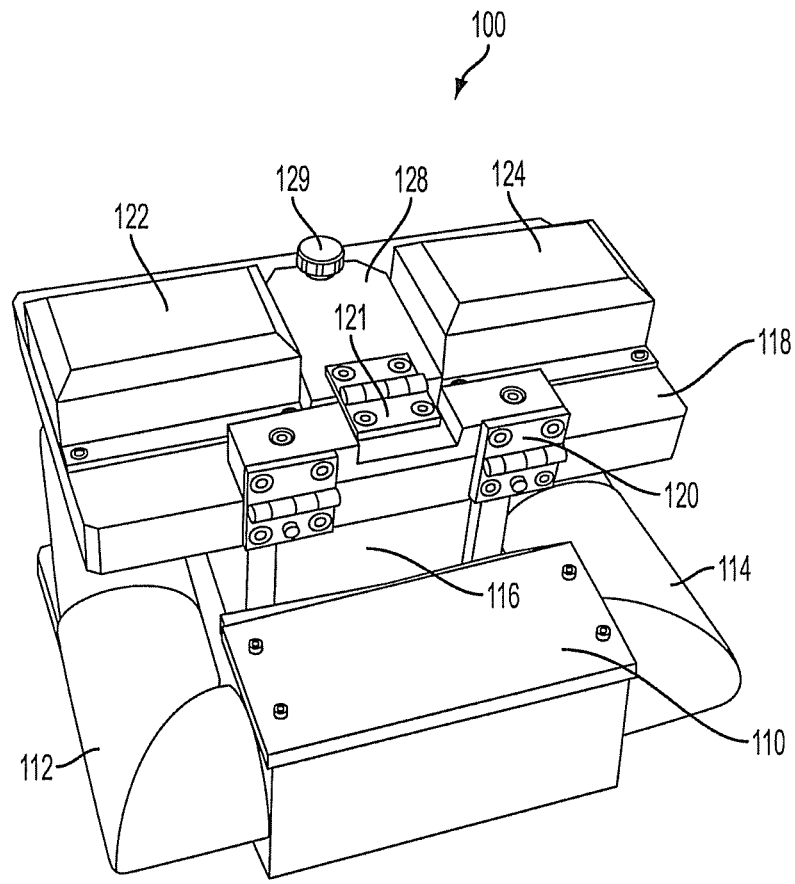
FIG. 1A illustrates a perspective view of a bottle and syringe warmer in accordance with one embodiment of the present invention.

FIG. 1A illustrates a perspective view of a bottle and syringe warmer 100 in the closed position in accordance with one embodiment of the present invention. Although bottle and syringe warmer 100 may be used to warm any suitable liquid for a variety of purposes, bottle and syringe warmer 100 is particularly advantageous for warming feedings for premature infants. Likewise, as previously noted, while syringes and small bottles are the most commonly used milk containers in the NICU setting, other containers are contemplated for use with the invention. In a similar vein, while the invention has found particular application in an NICU environment, it can be used or adapted for other breastmilk and related feeding applications. A "feeding" or "infant feed" as used throughout this description refers to an amount of breastmilk or other suitable liquid for infants, where the former may be housed in a variety of containers such as a bottle, a syringe, or a vial, for example.

To ensure health and proper growth, rapid weight gain is important for a premature infant. One way for a premature infant to gain weight rapidly is to feed the infant breastmilk at the correct temperature. Breastmilk contains important immunoglobulins, nutritional components, and vitamins. If overheated, these elements within the breastmilk will not remain intact; thus it is important to avoid overheating the breastmilk. Feeding a premature infant breastmilk, or related liquid-like formula, at the correct temperature also avoids placing any undue stress on the infant that may be present as a result of the temperature difference between the infant's body temperature and the temperature of the feeding. Moreover, the manner of feeding the premature infant may be highly circumscribed, such as the need to administer the milk at a very small rate, as through a syringe-type feeder.

As shown in FIG. 1A, bottle and syringe warmer 100 includes a heater 110, a first passage 112, a second passage 114, and a housing 116. A first lid 118 rests on top of first passage 112, second passage 114, and housing 116, effectively forming the closed position in FIG. 1A. First lid 118 pivots about at least one first hinge 120 to cover or leave open to ambient air first passage 112, second passage 114, and a chamber 136. A second lid 128 may be attached to first lid 118, and may comprise a knob 129 for manual manipulation.

Figure 1B:
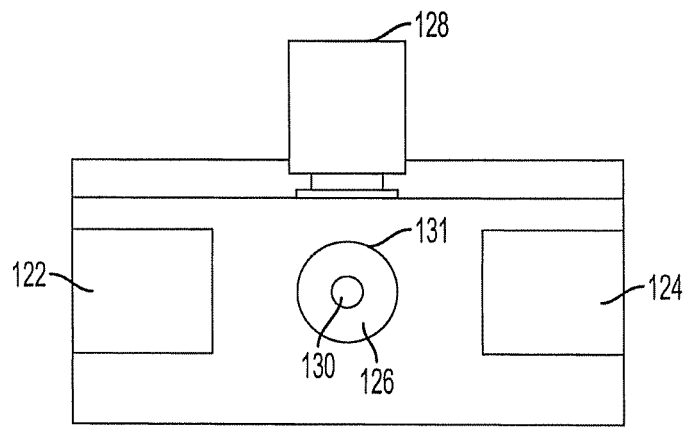
FIG. 1B illustrates a top view of a bottle and syringe warmer with an open lid in accordance with one embodiment of the present invention.

In the open lid position, as shown in FIG. 1B, first lid 118 comprises at least one first hinge 120, a first compartment 122, and a second compartment 124. Access port 126 comprises a hole 130. Second lid 128 is connected to first lid 118 with second hinge 121. Second lid 128 is positioned so that when the lid is in the closed position it covers hole 130.

Figure 2:
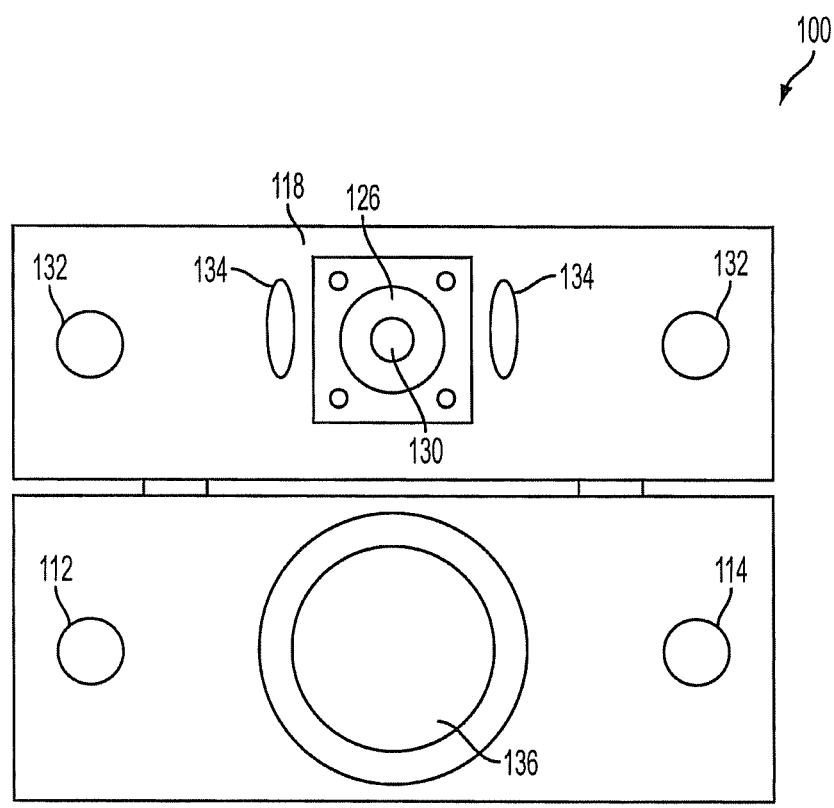
FIG. 2 illustrates a top view of a bottle and syringe warmer with an open cover in accordance with one embodiment of the present invention.

First compartment 122 and second compartment 124 are raised portions of lid 118. There are two openings per compartment, as shown in FIG. 2. A first opening 132 in each compartment is located so as to be in fluid communication with either first passage 112 or second passage 114 so that when lid 118 is in the closed position of FIG. 1A air flows from first passage 112 into first opening 132 of first compartment 122 and from first opening 132 of second compartment 124 into second passage 114. A second opening 134 in each compartment is located so that when lid 118 is closed, each second opening 134 allows for air to flow into and out from a chamber 136. FIG. 2 shows chambers 136 within housing 116.

In a situation in which a larger syringe is used, second lid 128 may be opened, and the larger syringe may be pushed through hole or orifice 130 so that the milk-containing portion of the syringe is in chamber 136. The plunger handle of the larger syringe extends outside of chamber 136. Access port 126 may hold the syringe to keep internal and external air flows separated. Hole or orifice 130 may be adjustable to accommodate various syringe sizes. One way to accomplish this would be to use an adjustable material, such as silicone, for access port 126.

First passage 112 is in fluid communication with heater 110 and with first compartment 122 of housing 116. Second passage 114 is in fluid communication with heater 110 and with second compartment 124 of housing 116. Each of first opening of first compartment 122 and second compartment 124 is in fluid communication with each of first passage 112 and second passage 114, respectively, and each of second opening 134 of first compartment 122 and second compartment 124 releases the air into chamber 136.

Bottle and syringe warmer 100 has the ability to be mounted on an IV pole. If mounted on an IV pole, bottle and syringe warmer 100 will have mechanisms to attach to the pole and to maintain the device in the upright position. This could be a clamp (not shown) affixed to the warmer 100. Having bottle and syringe warmer 100 attached to an IV pole that is bedside has many advantages. Warming and preparation of the milk may now be done at the bedside, allowing a nurse to spend a greater portion of his or her time near the baby, devoted to the infant's care. Additionally, every time milk is transferred from one area to another, an additional nurse is typically required to verify that the correct milk is going to the assigned patient. With bottle and syringe warmer 100 attached to the IV pole at a patient's bedside, this tedious step can be eliminated. Alternatively, bottle and syringe warmer 100 may be placed on a countertop.

Figure 3:
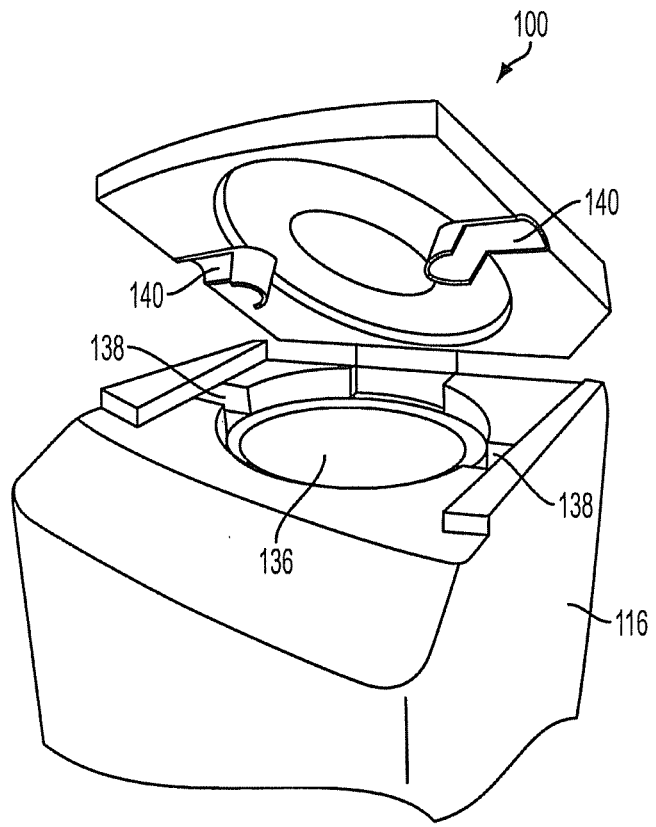
FIG. 3 illustrates a perspective view of an alternative mechanism for airflow within a bottle and syringe warmer.

FIG. 3 illustrates an alternative configuration to direct air into and out of chamber 136 through a conduit structure. Bottom pathways 138 are carved out of housing 116 on either side of chamber 136, and top pathways 140 are carved out of lid 118, so that when lid 118 is closed and lies flush with housing 116 each bottom pathway and top pathway mate to form a tunnel. First passage 112, not shown in FIG. 3, is within housing 116 and is in fluid communication with a first tunnel formed from a top pathway and a bottom pathway, not shown. Second passage 114 is also within housing 116 and is in fluid communication with a second tunnel, formed from a top pathway and a bottom pathway, not shown.

Figure 3A:
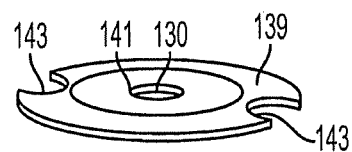
FIG. 3A is a syringe-receiving element for use with the same.

FIG. 3A shows a top or lid 139 that would further close chamber 136, and provide a flexible surface 141, with a hole or orifice 130 for receiving the syringe. Top or lid 139 has cut-outs 143 to accommodate pathways 140.

Preferably, heater 110 uses warm air forced convection as the primary mode of heat transfer. Alternate versions of heater 110 may employ either natural or forced convection, conduction, or radiation as the primary method to warm the milk. Bottle and syringe warmer 100 uses a non-liquid heating system to eliminate the infection risk and mess associated with using water for heat transfer.

The airflow within bottle and syringe warmer 100 may be conditioned. Conditioned air may be heated air. Alternatively, conditioned air may be cooled air. The airflow within bottle and syringe warmer 100 comprises a temperature that is altered by conditioning using either heater 110, a cooling mechanism, or both simultaneously.

Examples of reasons for cooling infant feed would be for temperature control, refrigeration prior to warming the liquid (storage), and post thawing. The conditioned airflow may be fully recirculating to minimize the power requirements necessary to heat or cool and maintain the air at the desired temperature. When the system is set up so that the air is recirculating, the airflow is substantially a closed or mostly closed system, wherein the air is conditioned to generate the desired heating or cooling effect. Closing the system reduces the power requirements to modify the air temperature. The conditioned airflow may be set up to be a partially recirculating, or a venting system. Airflow in a partially closed or open system would comprise ambient air introduction into the system. Ambient air at the ambient air temperature may be strategically introduced so as to quickly heat or cool the system air as desired, also helping reduce the power requirements to modify the air temperature.

The airflow temperature may be raised using a heating mechanism until the temperature of the airflow reaches a set temperature. The airflow temperature may then be maintained at the set temperature for a period of time. The length of the period of time may be determined by the user, or may be pre-set. To properly maintain the set temperature for a period of time, a cooling mechanism may be used to function in tandem with the heating mechanism. Both the cooling mechanism and the heating mechanism may operate at the same time. Alternatively, the heating mechanism and the cooling mechanism may alternate, so that only one of the mechanisms is operating at a time. After the designated period of time has elapsed, the temperature of the airflow may be reduced to a temperature that is less than the set temperature, using solely the cooling mechanism. In an alternative embodiment, once the temperature of the airflow achieves the set temperature, the airflow may be immediately cooled using the cooling mechanism to a temperature that is less than the set temperature.

Figure 11:
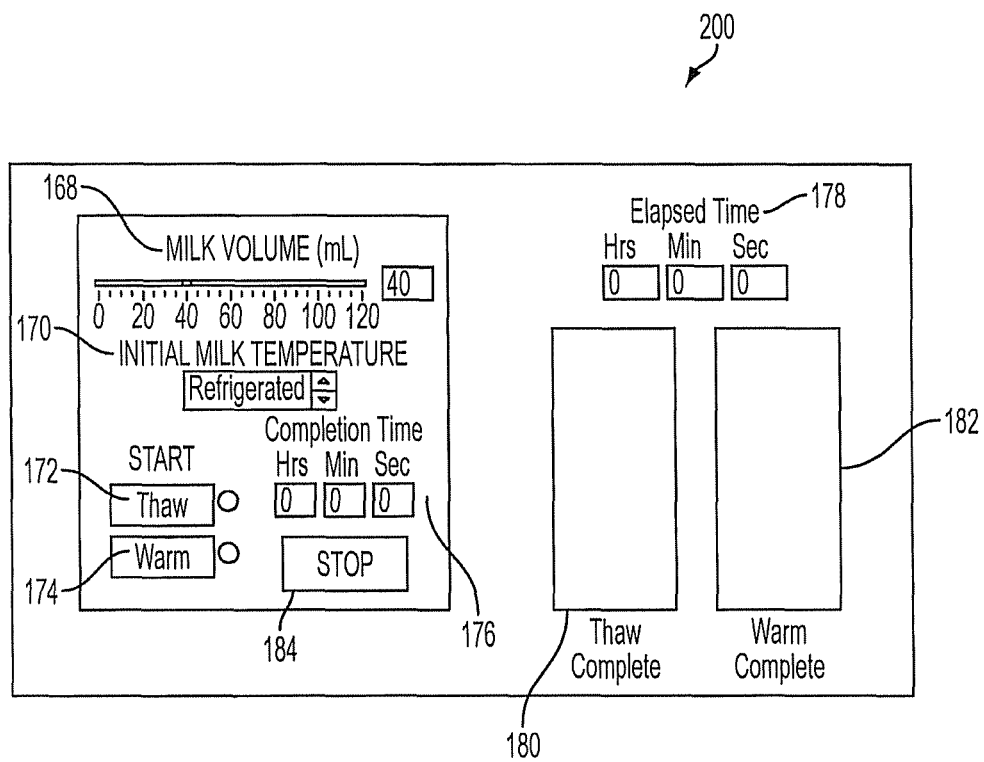
FIG. 11 illustrates an exemplary control screen according to an embodiment of the present invention.

Bottle and syringe warmer 100 may regulate the air temperature within chamber 136 using heating algorithms based on nurse entered parameters into a control panel 200, as shown in FIG. 11. For example, a nurse may manually enter milk parameters such as a volume of milk within a container parameter 168 or an initial milk temperature parameter 170. Other milk parameters could also comprise type or brand of container, and weight of the container and the milk inside the container, not shown in FIG. 11. Alternate versions may have one or more automated methods or sensors to provide these input variables. Temperature sensors may also be employed to detect the milk and/or container temperatures and thereby regulate and automate the conditioned air. After the nurse has input the desired parameters, the nurse may hit either a thaw button 172 or a warm button 174. The heating algorithms allow for customized heat profiles to minimize the time required to heat the milk. The heating algorithm may determine a completion time 176, and show completion time 176 on the control panel. On the control panel, an elapsed time bar 178 may show the time elapsed since the thawing or warming was initiated. Additionally, a thaw complete bar 180 and a warm complete bar 182 may be present on control panel 200. A stop button 184 may also be included so the nurse can manually stop the thawing or warming process.

Figure 17:
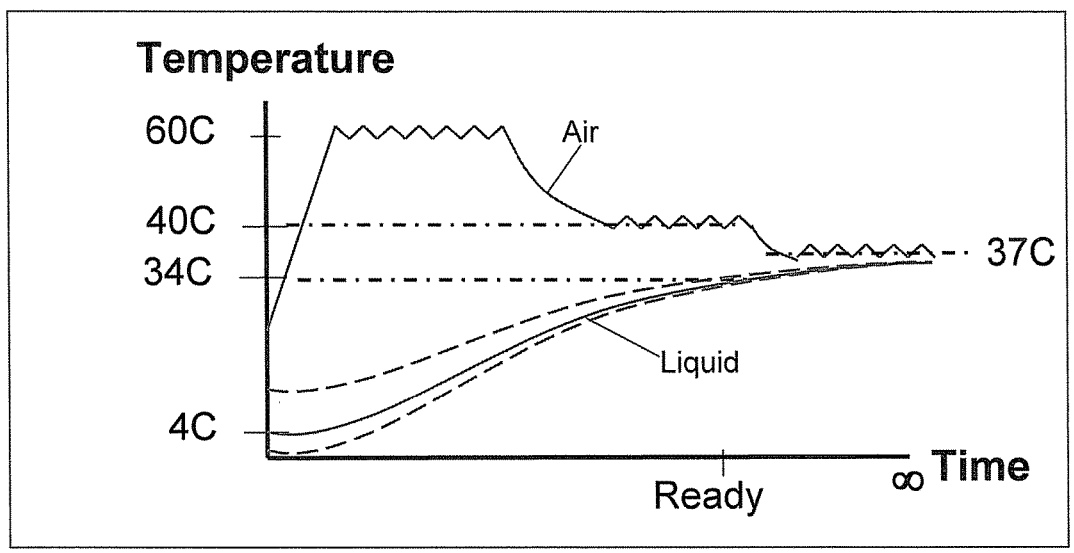
FIG. 17 is a diagram showing the temperature of the air and liquid over time.

In an exemplary embodiment, four heating profiles may be used based on the possible combinations of warming or thawing and the solid or liquid phases of milk. The first profile may be to warm refrigerated milk, the second profile to warm room temperature milk, the third profile to thaw frozen milk, and the fourth profile to warm frozen milk. An exemplary heating logic algorithm to warm refrigerated milk is shown in the diagram shown in FIG. 17. This diagram shows three temperature control zones for the heated air. Zone 1 may be a high heat zone, depicted in the diagram at 60° Celsius. Zone 2 is a low heat zone, depicted at 40° Celsius. Zone 3 is a ready hold zone, where the air is held at a set temperature, in the diagram below at 37° Celsius. The desired temperature for the liquid to be warmed to may be described as the "target" temperature, which in the diagram is 34° Celsius. The heating time calculations may be based on the volume of the liquid.

Temperature hold modes will maintain desired temperatures until the nurse is ready to use the milk. A maximum temperature may be set to as to not damage the composition of the breastmilk. The temperature limits may be based on University Western Australia research as disclosed in WO 2007/11267 A1 in order to ensure protection of proteins and other milk components by not overheating the milk. Based on this data, the air temperature itself could be held at a higher temperature that is determined to be safe, removing cross-contamination potential from a recirculating airflow.

Additionally, bottle and syringe warmer 100 may employ a cleaning cycle where the temperature limits are intentionally held or exceeded for a period of time in order to disinfect the device. Alternatively, an inline disinfecting agent, antimicrobial materials, filter, or UV light in the airflow may be used to disable or remove potential contaminants.

Heater 110 may be covered with a separate housing. Alternatively, housing 116 may cover the entire warming device, including heater 110.

Chamber 136 is large enough to accommodate a variety of sizes, shapes, and volumes of containers commonly used in the NICU. For example, chamber 136 may accommodate either a bottle or a syringe. Chamber 136 may comprise an airflow inlet into the interior of the chamber, which is in fluid communication with the conditioned airflow. Chamber 136 may be made to be infrared transparent. In this embodiment, an infrared transparent polymer would be used to manufacture the chamber.

Bottle and syringe warmer 100 typically includes a liner 146 to capture any spills and reduce potential contamination. Liner 146 is intended to be removed and changed out between patients and nurse shifts, but may be changed even more frequently. Portions of liner 146 may be used to direct airflow effectively around the bottle or syringe to maximize heat transfer. Liner 146 may also incorporate features to center the syringe or bottle in order to ensure effective and repeatable heat transfer and airflow.

Figure 4:
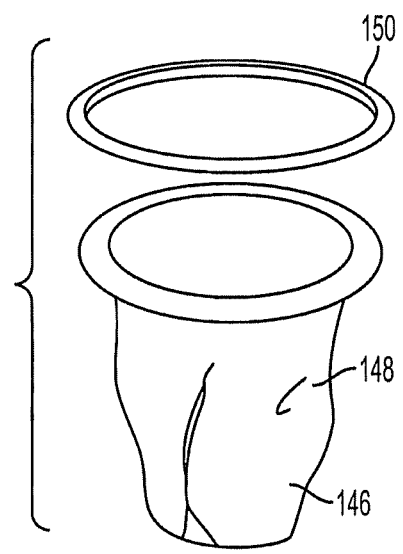
FIG. 4 illustrates a liner in accordance with one embodiment of the present invention.

Liner 146 may take on a variety of forms. FIG. 4 illustrates an exemplary liner 146. This liner comprises a malleable cup-shaped body 148 that can be inserted into chamber 136 of housing 116. Once liner 146 is put into place inside chamber 136, a rigid ring 150 is set on liner 146 to hold the liner in place within chamber 136.

Figure 5:
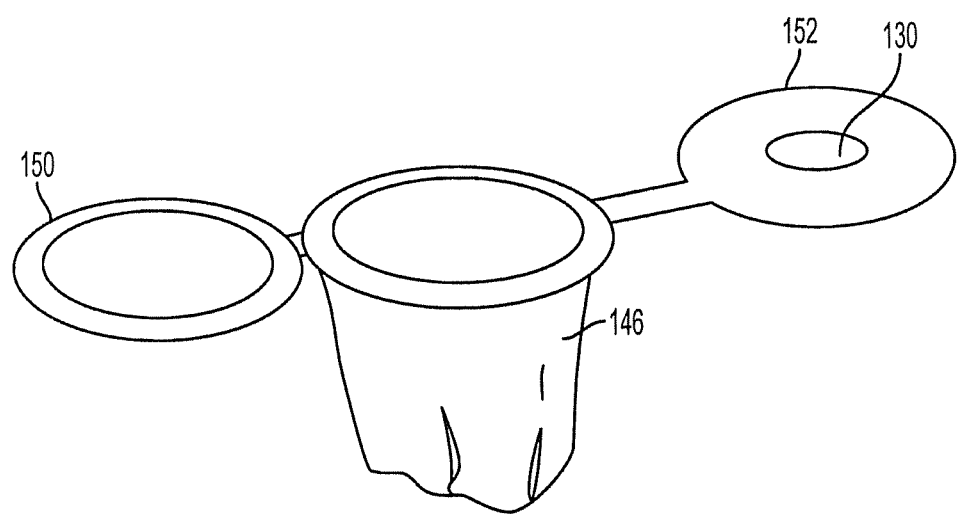
FIG. 5 illustrates a liner in accordance with one embodiment of the present invention.

FIG. 5 illustrates an exemplary liner configuration. Liner 146 is placed within a rigid ring, such as around chamber 136. Snap-ring 150 snaps down to secure the liner to the ring. Pass-through 152 is secured to seal a syringe inserted therein. Pass-through 152 may function as a lid for liner 146.

Figure 6A:
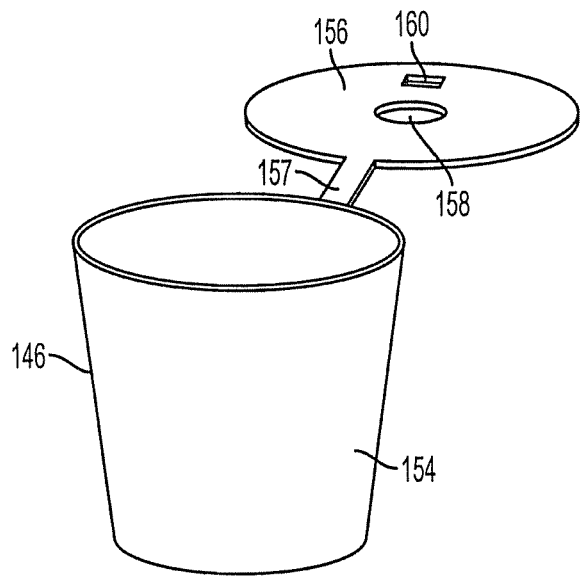
FIGS. 6A and 6B illustrate a liner in accordance with one embodiment of the present invention.
Figure 6B:
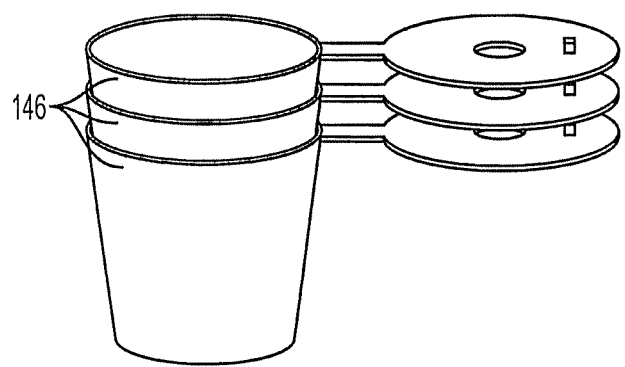

FIG. 6A illustrates another exemplary liner 146. In this embodiment, liner 146 has a rigid or semi-rigid cup-shaped body 154 that fits within chamber 136 of housing 116, as well as an attached top 156 via hinge 157. Attached top 156 comprises a hole or 158 and a slot 160. Lid 128 of housing 116 may have a hook that is insertable into slot 160 to mechanically attach liner 146 to bottle and syringe warmer 100. The liners may be stackable as shown in FIG. 6B. Hole 158 is the syringe pass-through and sealing feature.

Figure 7A:
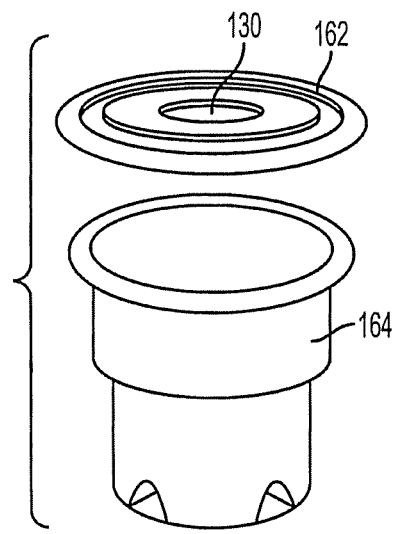
FIGS. 7A and 7B illustrate a liner in accordance with one embodiment of the present invention.
Figure 7B:
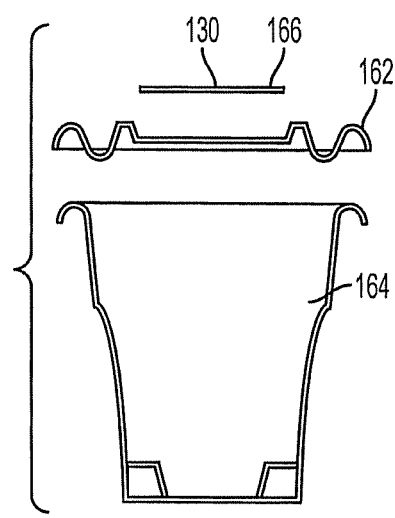
Figure 8:
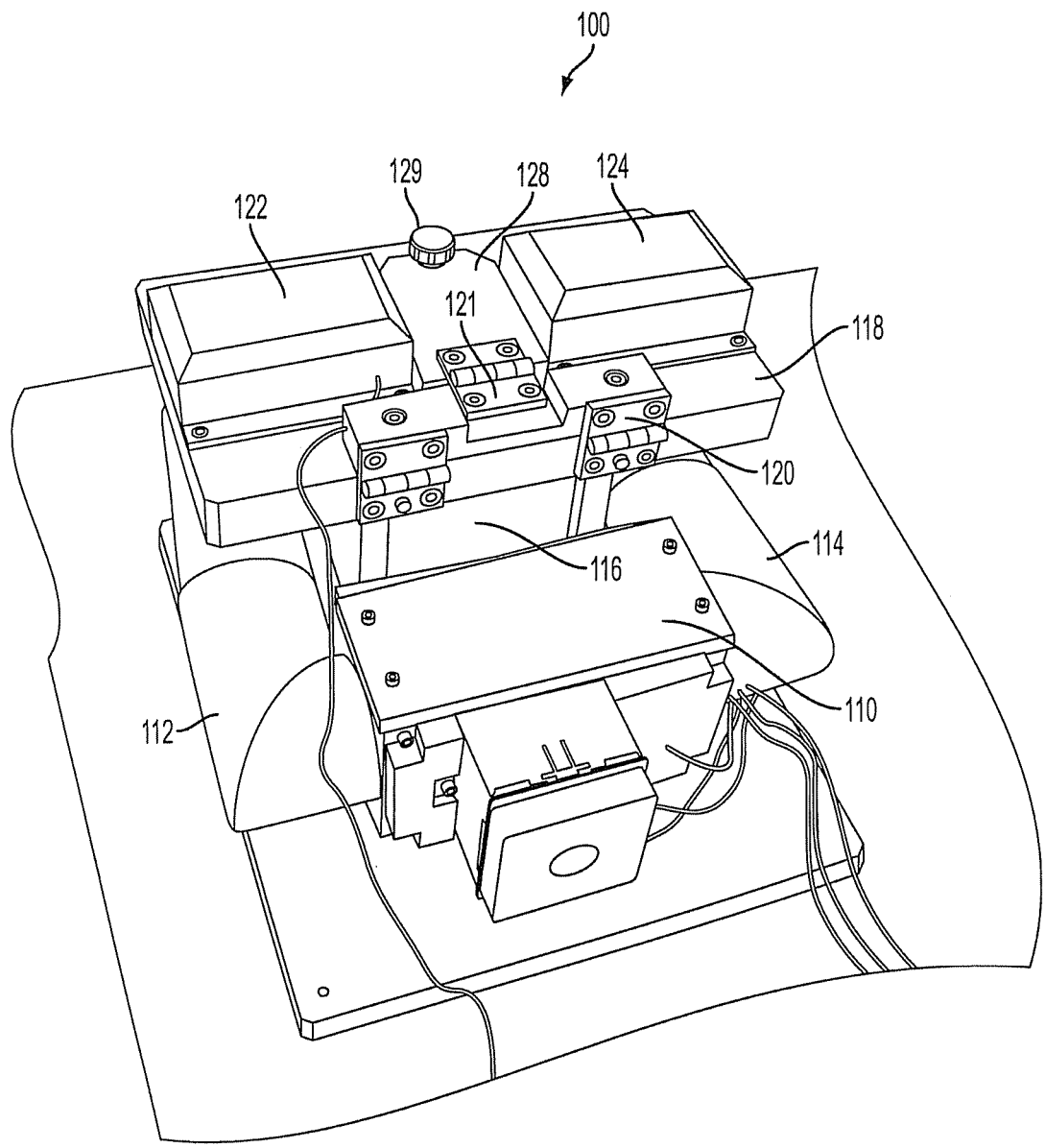
FIG. 8 illustrates a similar view as in FIG. 1A, of a prototype of an embodiment of the present invention.
Figure 9:
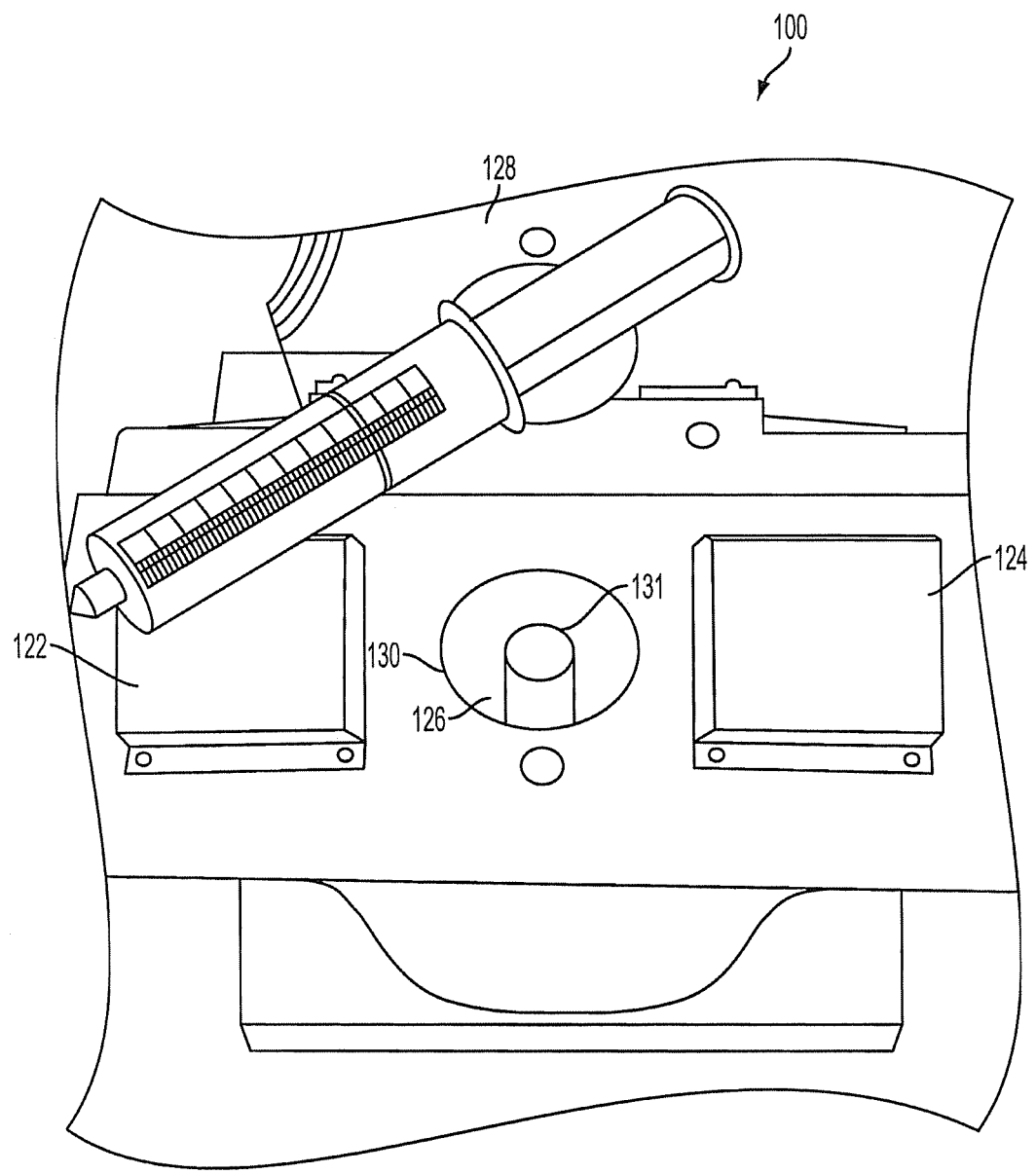
FIG. 9 illustrates a similar view as in FIG. 1B, of a prototype of an embodiment of the present invention.
Figure 10:
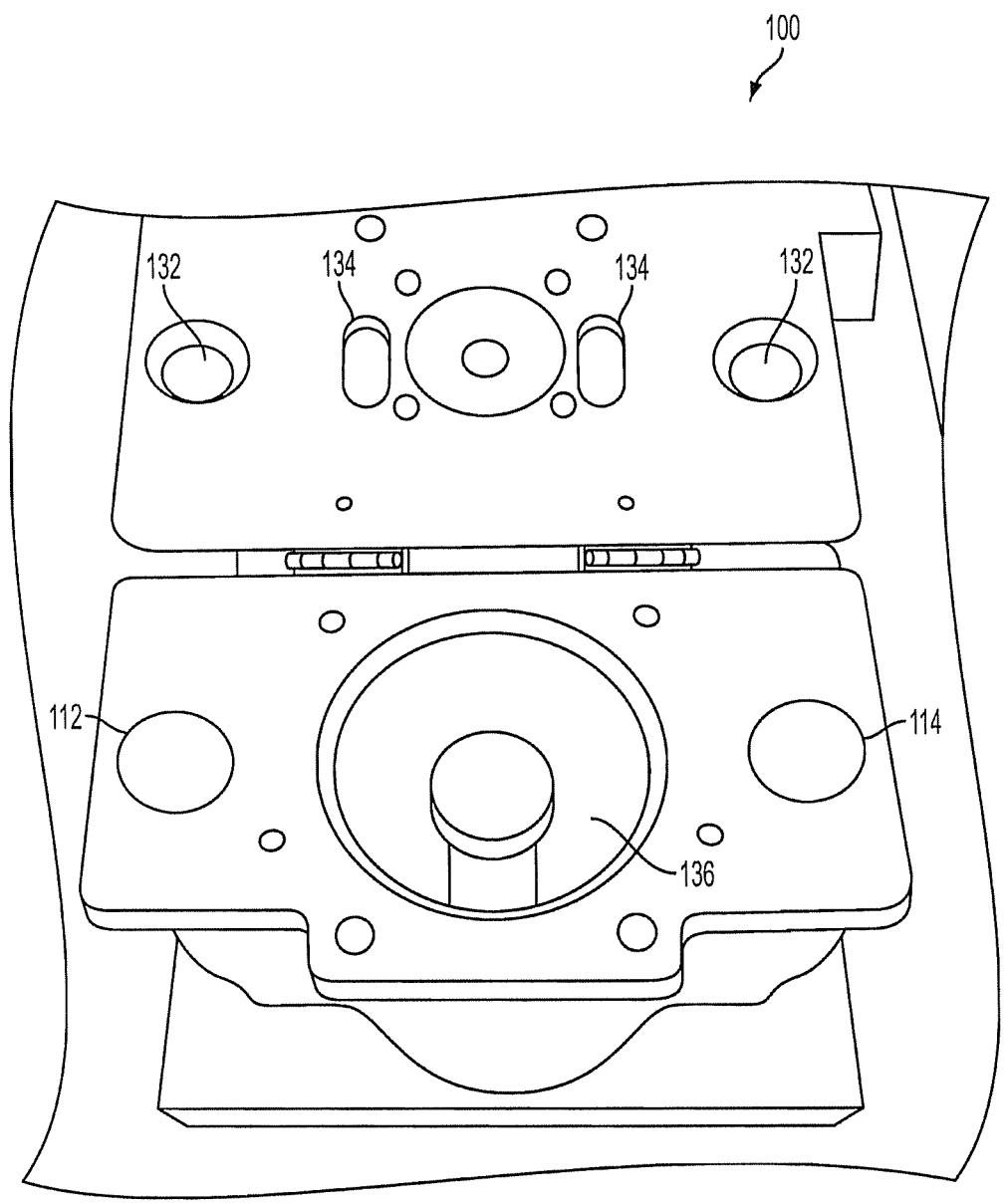
FIG. 10 illustrates a similar view as in FIG. 2, of a prototype of an embodiment of the present invention.

FIGS. 7A and 7B illustrate perspective and side views of a top 156 that may be placed on a rigid liner 164 that is then inserted into chamber 136. FIG. 7B also shows a separate disk 166 which is flexible and has hole 130 as a syringe pass-through feature. It would be captured in pass-through lid 162. Pass-through lid 162 would preferably have holes cut in the top to allow airflow into the chamber as in FIG. 3. As an alternative, rigid liner 164 may be one piece that incorporates the pass-through lid 162.

Bottle and syringe warmer may also comprise a multi-chamber unit. In this embodiment, a plurality of chambers is present in housing 116 instead of merely one chamber. In this embodiment, one chamber is designated for heating and thawing and the other chambers could be storage areas for the refrigeration or freezing of milk.

In operation, lid 118 of housing 116 is opened to reveal the interior of chamber 136. Liner 146 may be placed inside chamber 136 using any of the methods previously discussed to attach liner 146 to chamber 136. Next a bottle is placed inside liner 146. After the bottle is placed in liner 146, lid 118 is returned to the closed position, and a nurse may enter information into bottle and syringe warmer 100 describing the previously discussed parameters required for the heating algorithm. Heater 110 then heats air using forced convection. The heated air exits heater 110 and enters into first passage 112. The heated air then moves through first passage 112 into first compartment 122, and finally into chamber 136. While the conditioned air is within the interior of chamber 136, it is effectively heating the liquid inside the bottle. The air is able to exit chamber 136 via second compartment 124 and then through second passage 114, and may either exit to ambient air or return to heater 110 for re-circulation. A temperature sensor may provide control of the air temperature and monitor the heating profile.

If a syringe is to be heated in lieu of a bottle, access port 126 is used. A syringe detection sensor may be used to detect whether a syringe is being used instead of a bottle. After liner 146 has been secured within chamber 136, lid 118 may be returned to the closed position and lid 128 may be opened, revealing access port 126 and hole 130. A sensor may be used to determine when lid 118 is closed. The syringe may be inserted into hole 130, ensuring that the liquid containing portion of the syringe is within chamber 136. The heating process then begins as described in the example using a bottle.

Figure 12:
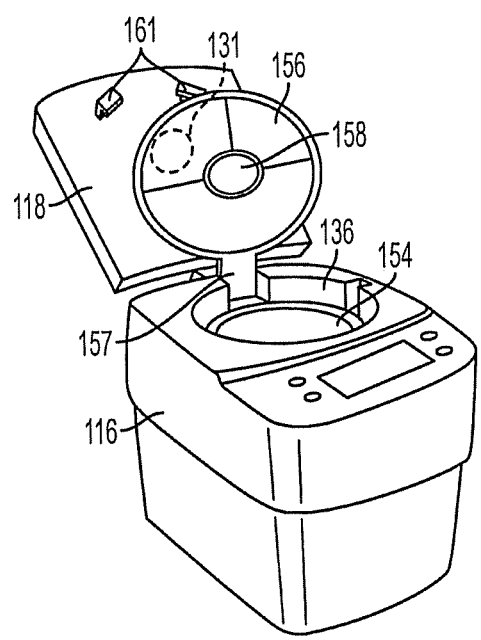
FIG. 12 is a perspective view of another embodiment of a bottle and syringe warmer with a liner mounted therein.

FIG. 12 is yet another embodiment of a warming apparatus particularly adapted for syringes and bottles, and very similar to that described with regard to FIG. 3. Here, housing 116 has a lid 118 that closes chamber or well 136. This embodiment uses a modified liner similar to that of FIG. 6A, having a body 154 and top 156 which is attached via a hinge 157. Hole or orifice 158 is again provided for use with a syringe or other small diameter container. Top 156 is thus made flexible at least in the area of this hole or orifice 158 for a sealing closure around the syringe.

The liner top 156 is held in place on housing lid 118, so as to open and close the liner body 154 as the lid 118 is opened and closed. Shown are a pair of clasps 161 that grip the front edge of top 156 for travel with the lid. Alternative mechanisms can be readily envisioned to keep top 156 in place with the lid. Note that orifice 131 (shown in dotted line) is formed in lid 118 and aligns with hole 158 for access to the chamber for a syringe with lid 118 closed. Lid may be made from an infrared opaque substrate.

It will be further understood that top 156 may have cut-outs formed therein similar to those of FIG. 3A if an air manifold like that of FIG. 3 was employed. It will be noted, however, that this and other of the liners described herein, could be made with the airflow designed to flow around the liner, rather than through it, e.g., the body of the liner is sized much smaller than the chamber diameter, with air routed between the liner and chamber interior wall. In that event, no openings for airflow need be provided in the body/top. This is not considered the most desirable way to make the invention, however, since heat transfer must then occur through the relative static air thereby maintained inside the liner.

Figure 13:
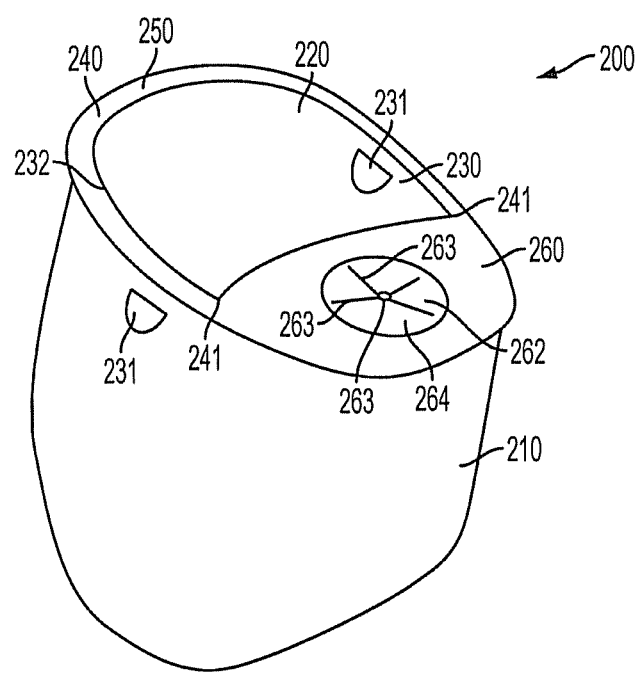
FIG. 13 is a perspective view of an exemplary liner according to one embodiment of the present invention.

FIG. 13 illustrates an exemplary liner 200 according to one aspect of the present invention. Liner 200 is intended to be changed out between patients and nurse shifts, but may be changed even more frequently. Portions of liner 200 may be used to direct airflow effectively around a container to maximize heat transfer. Liner 200 may also incorporate features to center the container in order to ensure effective and repeatable heat transfer and airflow.

In one embodiment, liner 200 comprises a bag or receptacle formed of a first material 210. First material may be a flexible polyethylene. The bag has an interior 220, an opening 230, and a plurality of pressure equalization holes 231. Pressure equalization holes 231 allow for air to flow between the outside of the bag and the bag interior so that the pressure inside the bag is equalized. Liner 200 may be formed from a first sheet being attached to a second sheet with a first seam, a second seam, and a third seam. The sheets effectively form the sides of liner 200.

Opening 230 includes a perimeter 232. Opening 230 may be sealed shut by attaching the first sheet to the second sheet along a fourth seam.

Liner 200 also comprises a rim portion 240 formed of a second material 250 and a section 260. Section 260 comprises a port 262.

Interior 220 has the purpose of containing liquid. Rim portion 240 may extend along the entire perimeter 232. Rim portion 240 may comprise an indented line that allows the rim portion to flex at the line, effectively creating a living hinge, or a hinge 241. Hinge 241 allows for the rim portion 240 to lie flat during manufacturing or storage of the liner, and then to flex as needed for insertion and use in the warmer. Section 260 may also be formed from second material 250, and may be integral with rim portion 240. Top section may cover at least a portion of opening 230, as shown in FIG. 13. The second material 250 used for rim portion 240 and section 260 may be manufactured from a rigid high density polyethylene. Second material 250 may be welded to first material 210.

Port 262 may serve as a pass-through for bottles, syringes, and the like. Port 262 may be a sphincter-like member. Port 262 may be flexible to accommodate various syringe sizes. One way to accomplish this would be to use a flexible third material 264, such as silicone, for port 262. The third material may be such that when pressure is applied to the material, the material deforms.

Third material 264 comprising port 262 may be molded so that there are no openings through the port, only frangible sections 263. Port 262 is then in a sealed state until a container such as a syringe is pressed against the third material 264 and breaks frangible portions 263, opening port 262.

Figure 14:
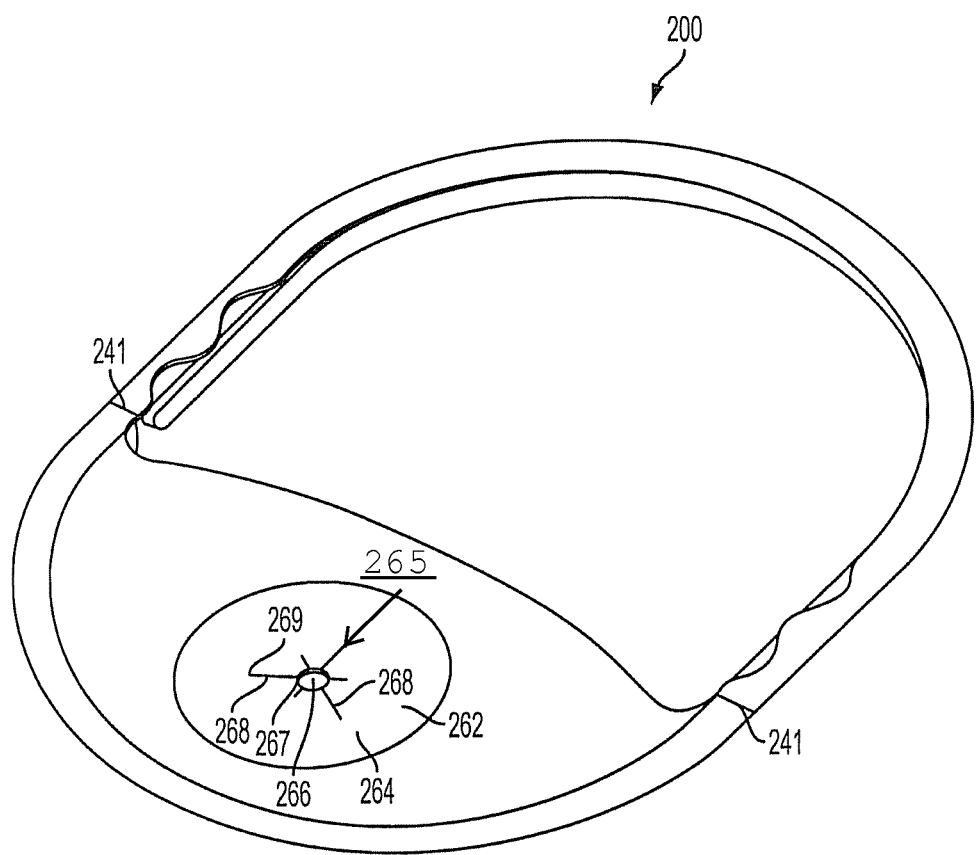
FIG. 14 is a top view of the liner of FIG. 13.

FIG. 14 shows a top view of liner 200. Alternatively, access port 262 may comprise a hole 266 and a plurality of slits 268, as shown in FIG. 14. Each slit comprises a first end 267 and a second end 269. First end 267 is located at the perimeter of hole 266. Each slit extends away from hole 266 such that second end 269 is at a location within port 262, as shown in FIG. 14. When pressure is applied to port 262, each of the plurality of slits 268 gives way, effectively creating a larger hole 266 through which a container may be pushed through. When a container is pushed through the hole, the plurality of slits 268 conforms to the sides of the container. The container may be a bottle. Alternatively, the container may be a syringe. The container may be any vessel that can house infant feed within. To accommodate a wide range of container diameters or sizes, the slits 268 may have a thin membrane 265 between them that tears for larger containers but stretches for smaller containers to provide for a better hold.

Figure 15:
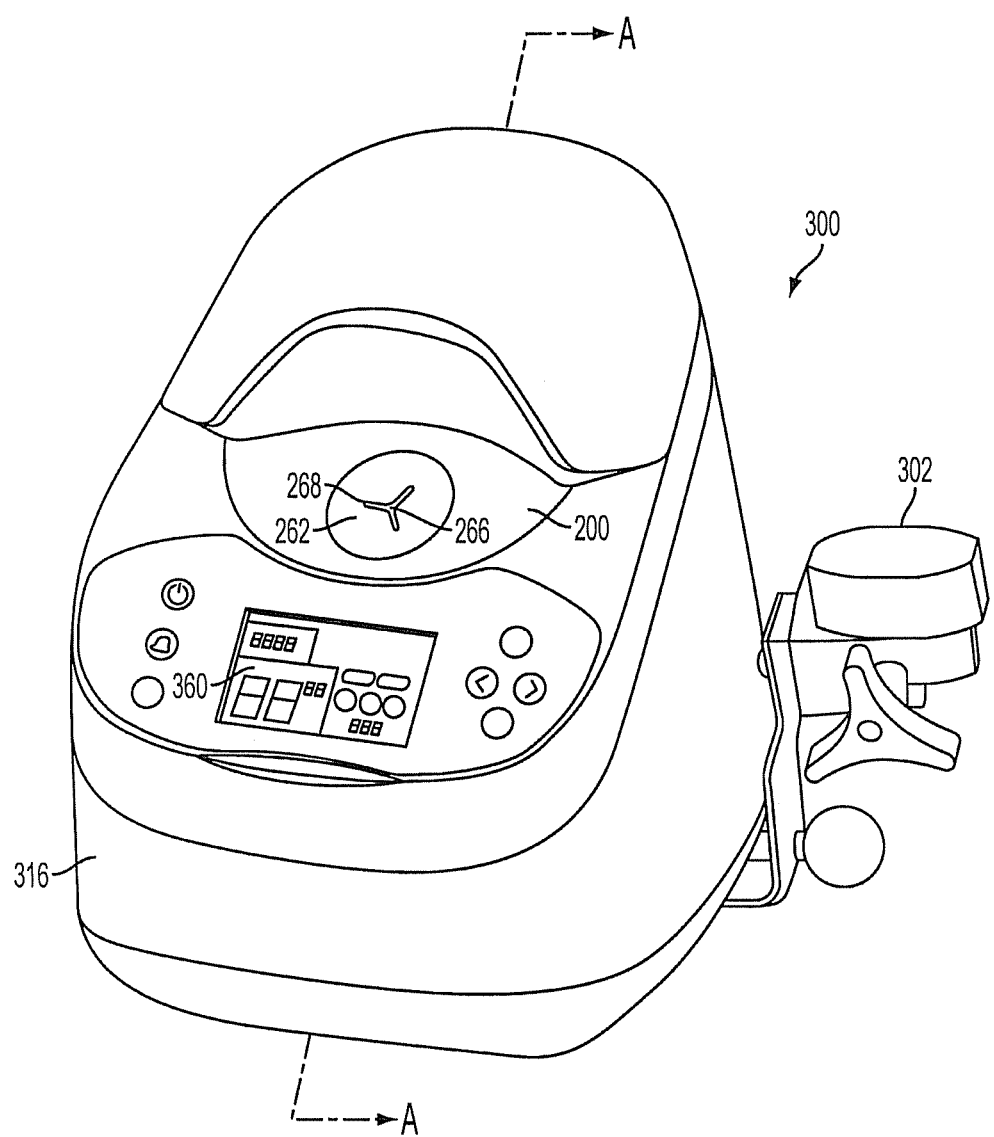
FIG. 15 is a perspective view of an exemplary bottle and syringe warmer according to one embodiment of the present invention.

FIG. 15 illustrates a perspective view of an exemplary liner 200 emplaced within a bottle and syringe warmer 300 in the closed position in accordance with one embodiment of the present invention. The infant feeding warming apparatus 300 in FIG. 15 comprises a mounting mechanism 302 attached to a housing 316 that may be used to mount infant feeding warming apparatus 300 to an IV pole. A display 360 shows the user settings and current status of the infant feed. A liner present sensor may be present on infant feeding warming apparatus 300 to ensure operation only with the liner installed.

Figure 16:
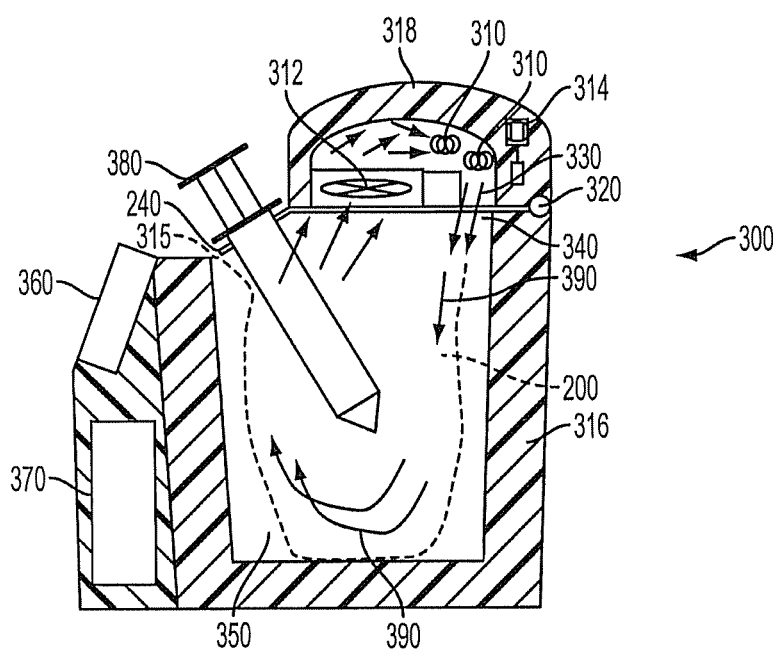
FIG. 16 is a cross-sectional view of the bottle and syringe warmer of FIG. 15.

FIG. 16 shows a cross-sectional view of the bottle and syringe warmer 300 of FIG. 15, taken at A-A. Infant feeding warming apparatus 300 comprises at least one heater 310, a fan 312, a vent mechanism 314, a housing 316, a lid 318, at least one hinge 320, an upper duct 330, a lower duct 340, a chamber 350, display 360, and a power supply 370. Housing 316 further comprises a housing lip 315.

In operation, lid 318 of housing 316 is opened to reveal chamber 350. Liner 200 may be placed inside chamber 350 by setting rim portion 240 on housing lip 315, as shown in FIG. 16. A container may then be inserted through opening 230 into the liner interior. Lid 318 is returned to the closed position, the closed position being shown in FIGS. 15 and 16, covering opening 230 of liner 200. If a container was not already emplaced in the liner, a container 380 such as a syringe, as shown, can be placed through port 262, ensuring that the liquid containing portion of the syringe is within chamber 350. In the alternative, container 380 may not be a syringe but may be a number of other containers used in the field. As an example, container 380 may be a vial.

The container may have one or more sides, a top and a bottom. Liner 200 is sized to receive the container therein, allowing for the container side or sides to be spaced from the side or sides of liner 200, such that airflow through liner 200 can pass around the side or sides of the container to thereby provide moving air around the container.

FIG. 16 also shows the path of air flow with arrows 390. Fan 312 blows the air through each heater 310, effectively heating the air. Alternatively, cooling devices may be present that cool the air that is blown by fan 312. The air then flows through the conduit structure: upper duct 330, lower duct 340, and into liner 200. The air is forced around container 380, providing moving air around the container. The air then moves up through fan 312. Air may enter or exit the system through vent mechanism 314.

A motion mechanism may be included to vibrate or mix the milk in the bottle or syringe during operation. The benefit of the motion mechanism would be to keep the milk components homogenous as well as aid in heat transfer, speeding up the warming process. This motion may be imparted by a mechanical system such as a shaker or orbital mixer. Additionally the motion may be imparted by the air circulation on the container already in use for the heat transfer.

Various exemplary embodiments have been described above. Those skilled in the art will understand, however, that changes and modifications may be made to those examples without departing from the scope and spirit of the present invention. And it should be noted that the above overview is meant to be illustrative, not limiting. That is, additional and/or different features may be present in some embodiments of the present invention.

The invention claimed is:

1. A liner configured to be used with an infant feeding thermal treatment system, the liner comprising:
   a flexible-receptacle defining an interior;
   a rim member having a first portion defining a receptacle opening for airflow from the thermal treatment system to pass into and then out of the interior,
   the rim member having a widened second portion extending from the first portion;
   a port formed in the widened second portion of the rim member such that the receptacle opening and the port are arranged eccentric to each other in the rim member, the port adapted to allow a container to be passed at least partially therethrough and into the receptacle interior; and
   at least one of a plurality of frangible sections and a plurality of slits arranged within the port such that each of the plurality of frangible sections and the plurality of slits have a first end that terminates in a center of the port and a second end extending radially away from the center of the port, each of the plurality of frangible sections and the plurality of slits configured to conform to the container when the container is pushed through the port.

2. The liner of claim 1, wherein heated air is conveyable into the receptacle interior to warm a container comprising infant feed placed therein.

3. The liner of claim 1, wherein the receptacle is a bag, and wherein the container is a syringe.

4. The liner of claim 1, wherein the liner is disposable and configured to be used with an apparatus configured for circulating a fluid medium through the liner, the liner comprising:
   a material defining the interior of the liner within which the airflow is able to be circulated and contained;
   the material being attached to the rim member, the rim member being mountable to the apparatus and when mounted thereby held in place for use, the receptacle opening being closed by the apparatus, when mounted, to all but the circulating airflow in use; and
   the receptacle opening defined in the rim member adapted to receive a vessel therein so as to pass the vessel into the interior when the liner is mounted in the apparatus in use.

5. The liner of claim 1, the first portion being in a first plane, and the widened second portion extending from the first portion in a second plane of the rim member.

6. The liner of claim 1, wherein the receptacle is formed of a first material and the first portion of the rim member is formed of a second material.

7. The liner of claim 6, wherein the second portion of the rim member is formed of the second material.

8. The liner of claim 1, wherein the first portion of the rim member comprises an indented line allowing the rim portion to flex at the line and allowing the rim portion to lie flat during manufacturing or storage of the liner and then to flex as needed for insertion into the thermal feeding treatment system.

9. The liner of claim 1, wherein at least a part of the receptacle is designed to cooperate with a detector for detecting when the liner is in place within a chamber.

10. The liner of claim 1, comprising:
    a material forming a liner body defining the receptacle and the receptacle opening into which a container of infant feed is receivable, the liner being adapted to be supported within a liner support structure so as to be selectively disposed to receive the airflow within the receptacle interior, the liner constructed to receive the airflow being at a temperature including temperatures that differ from an initial temperature of the infant feed.

* * * * *